United States Patent

Ninomiya et al.

[11] Patent Number: 5,882,675
[45] Date of Patent: Mar. 16, 1999

[54] PERCUTANEOUS ABSORPTION PREPARATION

[75] Inventors: Kazuhisa Ninomiya; Shoichi Tokuda; Yasuhiro Fukushima, all of Osaka, Japan

[73] Assignee: Nitto Denko Corporation, Osaka, Japan

[21] Appl. No.: 812,545

[22] Filed: Mar. 7, 1997

[51] Int. Cl.$^6$ ................................................. A61F 13/02
[52] U.S. Cl. ........................... 424/448; 424/449; 424/489
[58] Field of Search ................................. 424/448, 449, 424/489

[56] References Cited

U.S. PATENT DOCUMENTS

| | | | |
|---|---|---|---|
| 3,598,123 | 8/1971 | Zaffaroni | 128/268 |
| 4,889,721 | 12/1989 | Ueda | 424/448 |
| 5,028,435 | 7/1991 | Katz | 424/484 |
| 5,077,055 | 12/1991 | Mueller et al. | |
| 5,556,635 | 9/1996 | Istin | 424/448 |
| 5,582,836 | 12/1996 | Carli | 424/449 |

FOREIGN PATENT DOCUMENTS 0711551  5/1996  European Pat. Off. .
2719770  11/1995  France .

*Primary Examiner*—D. Gabrielle Brouillette
*Attorney, Agent, or Firm*—Sughrue, Mion, Zinn, Macpeak & Seas, PLLC

[57] ABSTRACT

The present invention provides a percutaneous absorption preparation which has excellent pressure-sensitive adhesive characteristics and exerts excellent percutaneous absorption property. A crosslinking agent is added to a solution of an acrylic copolymer prepared by copolymerizing a (meth) acrylic acid alkyl ester with a functional monomer, and the acrylic copolymer is partially crosslinked. A composition containing the crosslinked acrylic copolymer is pulverized to prepare a pressure-sensitive adhesive solution comprised of the acrylic copolymer containing crosslinked acrylic copolymer particles. Thereafter, a drug for percutaneous absorption use, a percutaneous penetration enhancer are added to the pressure-sensitive adhesive solution, thereby producing the percutaneous absorption preparation.

7 Claims, 1 Drawing Sheet

, 
PERCUTANEOUS ABSORPTION PREPARATION

FIELD OF THE INVENTION

The present invention relates to a percutaneous absorption preparation and a production method thereof. Particularly, it relates to a percutaneous absorption preparation which is adhered to the skin to effect continuous administration of a drug from the skin into the living body, and to a production method thereof.

BACKGROUND OF THE INVENTION

In recent years, percutaneous absorption adhesive preparations for external use such as various types of cataplasmas and tapes have been developed using ointment bases and pressure-sensitive adhesives, as percutaneous absorption preparations for use in the administration of drugs into the living body through the skin.

As the method for effectively releasing drugs from these adhesion type percutaneous absorption preparations and efficiently effecting their absorption by the living body from the skin, various methods have been proposed in which, for example, concentration of the drug to be contained is increased or a percutaneous penetration enhancer is jointly used. These methods improve percutaneous absorption of drugs, but the pressure-sensitive adhesive property of the percutaneous absorption preparation is frequently reduced to cause a so-called stringiness and adhesive residue on the skin surface.

As means for resolving these problems, various methods have been proposed, such as a method in which fine powder silica is added to a pressure-sensitive adhesive (JP-A-2-295565; the term "JP-A" as used herein means an "unexamined published Japanese patent application") or a method in which pressure-sensitive characteristics are controlled by making an ointment base into gel form through crosslinking of a pressure-sensitive adhesive (JP-A-3-220120).

Of these methods, the method in which fine powder silica is added to a pressure-sensitive adhesive is used in various field, because it is generally known that fine powder silica acts as a rheology agent to change flow characteristics of pressure-sensitive adhesives.

However, the method in which fine powder silica is added cannot improve pressure-sensitive adhesive characteristics in some cases depending on the formulation composition and formulation method of pressure-sensitive adhesives. Particularly, decrease in the viscosity of pressure-sensitive adhesives cannot be prevented when a polar substance such as polyethylene glycol is added in a large amount as a percutaneous penetration enhancer.

On the other hand, the method in which entire portion of a pressure-sensitive adhesive is crosslinked by external crosslinking to make it into gel form is markedly excellent in view of the point that the pressure-sensitive adhesive characteristics can be controlled even when a percutaneous penetration enhancer and other additives are used in a large amount.

This method, however, also cannot be used in the case where the percutaneous absorption preparation contains a substance having a crosslinking inhibition action, because the pressure-sensitive adhesive cannot fully be crosslinked. In particular, when a generally and frequently used multifunctional isocyanate is used as a crosslinking agent, addition of a drug or additive having a hydroxyl group, an amino group, a carboxyl group or a mercapto group to the pressure-sensitive adhesive causes crosslinking inhibition. For the reason, the drugs and additives having these functional groups cannot be used.

In addition, techniques in which a percutaneous absorption preparation is produced by making a pressure-sensitive adhesive into granular form are disclosed for example in JP-B-58-12255 (the term "JP-B" as used herein means an "examined Japanese patent publication") and JP-B-58-23367, but these techniques have a difficulty in obtaining appropriate pressure-sensitive adhesive characteristics in the case where a percutaneous penetration enhancer and other additives are used in a large amount.

SUMMARY OF THE INVENTION

In view of the above, the inventors of the present invention have conducted intensive studies, with the aim of developing a skin adhesion type percutaneous absorption preparation which has excellent pressure-sensitive adhesive characteristics, does not generate skin irritation and exerts excellent percutaneous absorption, and found that the aforementioned problems can be resolved by blending a pressure-sensitive adhesive with crosslinked acrylic copolymer particles prepared by crosslinking and pulverizing an acrylic copolymer. The present invention has been accomplished on the basis of this finding.

According to the present invention, there is provided a percutaneous absorption preparation comprising a backing having formed on one side thereof a pressure-sensitive adhesive layer containing a drug for percutaneous absorption use, wherein the pressure-sensitive adhesive layer comprises an acrylic copolymer containing therein crosslinked acrylic copolymer particles formed by subjecting an acrylic copolymer to crosslinking and pulverization.

Furthermore, according to the present invention, there is provided a method for producing a percutaneous absorption preparation comprising a backing having formed on one side thereof a pressure-sensitive adhesive layer containing a drug for percutaneous absorption use, which comprises:

adding a crosslinking agent to a solution of an acrylic copolymer to effect crosslinking, subjecting the resulting solution to pulverization to prepare a pressure-sensitive adhesive solution containing an acrylic copolymer and crosslinked acrylic copolymer particles, adding a drug for percutaneous absorption use and optionally a percutaneous penetration enhancer and other additives to the pressure-sensitive adhesive solution, and coating the backing with the resulting pressure-sensitive adhesive solution to form a pressure-sensitive adhesive layer.

Other objects and advantages of the present invention will be made apparent as the description progresses.

DETAILED DESCRIPTION OF THE INVENTION

Figure 1:
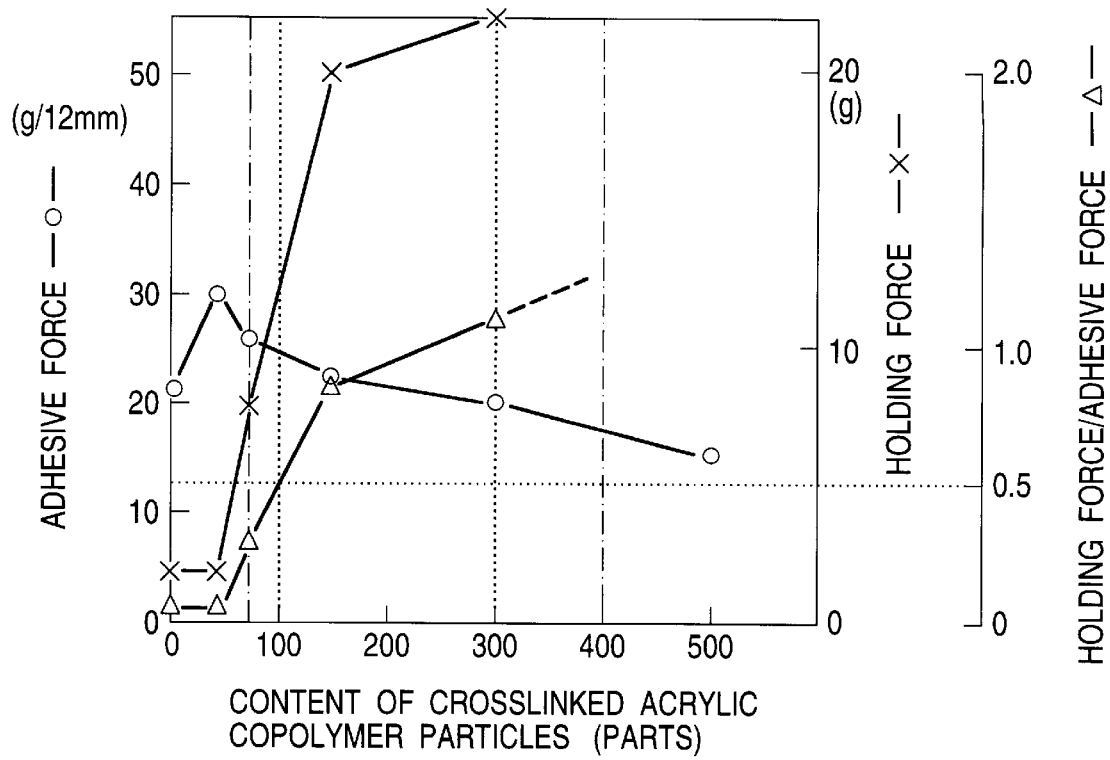
FIG. 1 is a graph showing a relationship between containing ratio of crosslinked acrylic copolymer particles and various physical property values of each percutaneous absorption preparation.

It is desirable that the backing to be used in the present invention is made of such a material that a drug for percutaneous absorption use and a percutaneous penetration enhancer contained in the pressure-sensitive adhesive layer do not pass through the backing and escape from its back side surface to cause reduction of the contents. Examples thereof include a single film such as of polyester, nylon, Saran (available from Dow Chem), polyethylene, polypropylene, polyvinyl chloride, ethylene-vinyl acetate copolymer, polytetrafluoroethylene, Surlyn (available from Du Pont), and a metal foil or a laminate film thereof.

Also, in order to improve adhesive force (anchor force) between the backing and a pressure-sensitive adhesive layer which will be described later, it is desirable to make the backing into a laminate film of a non-porous film made of the aforementioned material with woven or non-woven fabric. In that case, it is preferred that the laminate film has a thickness of from 10 to 200 $\mu$m.

Alternatively, when characteristics as a single film are desired, it is desirable to subject a single film as the backing to a so-called undercoat treatment. In that case, it is preferred that the single film has a thickness of from 1 to 100 $\mu$m.

The conventional acrylic pressure-sensitive adhesives can be used as the acrylic copolymer to be used in the present invention. The acrylic copolymer generally has a number average molecular weight of 10,000 to 300,000. The amount of the acrylic copolymer to be contained in the pressure-sensitive adhesive layer is generally from 4 to 50% by weight, preferably from 5 to 35% by weight based on the weight of the pressure-sensitive adhesive layer.

The acrylic copolymer to be used in the pressure-sensitive adhesive layer of the present invention can be obtained, for example, by using a (meth)acrylic acid alkyl ester, which is commonly used in acrylic pressure-sensitive adhesives, as the main monomer component and copolymerizing it with a functional monomer.

Examples of the (meth)acrylic acid alkyl ester include (meth)acrylic acid alkyl esters having straight or branched-chain $C_{4-13}$ alkyl groups such as butyl, pentyl, hexyl, heptyl, octyl, nonyl, decyl, undecyl, dodecyl and tridecyl, and one or two or more (meth)acrylic acid alkyl esters can be used.

In addition, the (meth)acrylic acid alkyl ester is not particularly limited to the above examples, and a (meth)acrylic acid alkyl ester having a straight or branched-chain alkyl group of 1 to 3 carbon atoms or a (meth)acrylic acid alkyl ester having a straight or branched-chain alkyl group of 14 or more carbon atoms may be used in combination with a (meth)acrylic acid alkyl ester having a straight or branched-chain alkyl group of 4 to 13 carbon atoms.

Examples of the functional monomer copolymerizable with these (meth)acrylic acid alkyl esters include polar monomers and vinyl monomers.

Examples of the copolymerizable polar monomer include a carboxyl group-containing monomer such as (meth)acrylic acid, itaconic acid, maleic acid, maleic anhydride and crotonic acid, a sulfoxyl group-containing monomer such as styrenesulfonic acid, allylsulfonic acid, sulfopropyl (meth)acrylate, (meth)acryloyloxynaphthalenesulfonic acid, and acrylamidemethylpropanesulfonic acid, a hydroxy group-containing monomer such as (meth)acrylic acid hydroxyethyl ester and (meth)acrylic acid hydroxypropyl ester an amido group-containing monomer such as (meth)acrylamide, dimethyl(meth)acrylamide, N-butylacrylamide, N-methylol(meth)acrylamide, and N-methylolpropane(meth)-acrylamide, an alkylaminoalkyl group-containing monomer such as (meth)acrylic acid aminoethyl ester, (meth)acrylic acid dimethylaminoethyl ester and (meth)acrylic acid tert-butylaminoethyl ester, a (meth)acrylic acid alkoxyalkyl ester such as (meth)acrylic acid methoxyethyl ester and (meth)acrylic acid ethoxyethyl ester, an alkoxy group (or oxide bonding to side chain)-containing (meth)acrylic acid ester such as (meth)acrylic acid tetrahydrofurfuryl ester, (meth)acrylic acid methoxyethylene glycol ester, (meth)acrylic acid methoxydiethylene glycol ester and (meth)acrylic acid methoxypolyethylene glycol ester, and (meth)acrylonitrile. These monomers may be used alone or as a mixture of two or more to effect copolymerization.

Examples of the vinyl monomer include a vinyl ester such as vinyl acetate and vinyl propionate, and a vinyl monomer having a nitrogen atom-containing hetero ring such as N-vinyl-2-pyrrolidone, methylvinylpyrrolidone, vinylpyridine, vinylpiperidone, vinylpyrimidine, vinylpiperazine, vinylpyrazine, vinylpyrrole, vinylimidazole, vinylcaprolactam and vinyloxazole. These monomers may also be used alone or as a mixture of two or more to effect copolymerization.

One kind or two or more kinds of the polar monomers and vinyl monomers can be copolymerized with the (meth)acrylic acid alkyl ester, but it is desirable to use a carboxyl group-containing monomer, a hydroxy group-containing monomer, an amido group-containing monomer, a (meth)acrylic acid alkoxyalkyl ester or an alkoxy group (or oxide bonding to side chain)-containing (meth)acrylic ester as the copolymerization component in the polymerization, because they have functional groups which become crosslinking points at the time of the crosslinking treatment and can improve cohesive force by increasing glass transition temperature of the acrylic copolymer. In addition, when the improvement of cohesive force and drug solubility is taken into consideration, it is desirable to use vinyl esters or vinyl monomers having a nitrogen atom-containing hetero ring in the copolymerization.

The amount of these copolymerizable polar monomers and/or vinyl monomers to be used in the copolymerization can be arbitrarily set to adjust cohesive force of the acrylic copolymer-based pressure-sensitive adhesive layer or solubility of a drug when included, but it is generally 50% by weight, preferably from 2 to 40% by weight.

The acrylic copolymer can be synthesized according known methods, for example, referring to "Kobunshi Jikkengaku Kouza 10 (High Molecules Experimentation Course 10)", published in Japan, Polymerization and Depolymerization Reaction, 1.3. Solution Polymerization (p.13), ii) Polymerization in a Three-Necked Flask.

The crosslinked acrylic copolymer particles take roles in preventing outflow of the percutaneous penetration enhancer which will be described later, imparting cohesive force to the pressure-sensitive adhesive layer, preventing stringiness, and imparting shape-keeping property to the pressure-sensitive adhesive layer. They also take a role in controlling release characteristics of the drug contained.

As the acrylic copolymer to be used in preparing the crosslinked acrylic copolymer particles, the same aforementioned acrylic copolymer as that to be contained in the pressure-sensitive adhesive layer can be used.

The crosslinking reaction for the preparation of the crosslinked acrylic copolymer particles can be effected by carrying out a physical crosslinking treatment in which irradiation with radiation such as ultraviolet rays or electron beam is effected or a chemical crosslinking treatment in which a crosslinking agent such as a multifunctional compound (e.g., a multifunctional isocyanate, an organic peroxide, an organic metal salt, a metal alcoholate, a metal chelate compound, a divinyl compound, an epoxy compound and melamine) is used.

From the point of view of reactivity, workability and the like, it is desirable to carry out a chemical crosslinking treatment using a trifunctional isocyanate, a metal alcoholate comprised of titanium or aluminum or a metal chelate compound. The amount of the crosslinking agent which can be used in the chemical crosslinking reaction is preferably from 0.01 to 2.0 parts by weight based on 100 parts by weight of the acrylic copolymer. In addition, when these crosslinking agents are used, it is desirable to use (meth) acrylic acid as the functional monomer in view of the crosslinking reactivity.

In a production method of the crosslinked acrylic copolymer particles, the aforementioned acrylic copolymer and the aforementioned crosslinking agent are uniformly stirred in an appropriate solvent such as an organic solvent, and the mixture is stored as such at a temperature of 50° to 80° C. until it is solidified by crosslinking into a gel form, or an acrylic copolymer solution to which a crosslinking agent is added is made into a film using a coating machine which is commonly used in the production of pressure-sensitive adhesive tapes, and the film is subjected to heat aging to effect crosslinking solidification.

The crosslinked and solidified acrylic copolymer composition is pulverized using a pulverizer to obtain crosslinked acrylic copolymer particles. Simultaneously with or prior to the pulverization, the crosslinked and solidified acrylic copolymer composition is diluted to a desired concentration by adding an appropriate solvent. Useful examples of the pulverizer include Gorator (trade name, manufactured by Nittetsu Mining Co., Ltd.), Disintegrator (trade name, manufactured by Komatsu Zenoah Co.), T. K. Cutruder (trade name, manufactured by Tokushu Kika Kogyo Co., Ltd.). In addition to these pulverizers, emulsifying or dispersing apparatuses such as TK Homomixer (trade name, manufactured by Tokushu Kika Kogyo K. K.) and the like can also be used. Of these, it is desirable to use Gorator, Disintegrator or T. K. Cutruder from the viewpoint of the treatment capacity. After pulverization is effected using one pulverizer such as Gorator, if necessary, subsequent pulverization may be effected using the other pulverizer such as a homomixer.

The particle size of the crosslinked acrylic copolymer particles varies depending on the dilution solvent. For example, in the case where the concentration of the crosslinked particles is adjusted to 1% by weight using ethyl acetate as a solvent, the size of the particles swelled with the solvent is preferably controlled to from 0.5 to 50 $\mu$m, more preferably from 1 to 20 $\mu$m. If the particle size is smaller than 0.5 $\mu$m, there is a possibility that no adding effects of the crosslinked particles are exhibited and reduction of cohesive force of the pressure-sensitive adhesive layer and generation of stringiness are caused. If it is larger than 50 $\mu$m, there is a possibility of deteriorating coating property to the backing, thereby resulting in streaked coating, irregular coat film surface, uneven thickness and poor appearance of the coat film after drying.

The thus-obtained crosslinked acrylic copolymer particles may be collected by an appropriate method and mixed with other acrylic copolymer solution.

The crosslinked acrylic copolymer particles may be contained in the pressure-sensitive adhesive layer in an amount of generally from 70 to 400 parts by weight, preferably from 100 to 300 parts by weight, based on 100 parts by weight of the acrylic copolymer. If the amount thereof is smaller than 70 parts by weight, there is a possibility that no significant adding effects of the crosslinked particles are exhibited and reduction of cohesive force and generation of stringiness are caused. If it is larger than 400 parts by weight, reduced adhesive force of the pressure-sensitive adhesive layer, poor adhesion to the skin surface and reduced anchor force between the layer and the backing may be caused. It is preferred that the crosslinked particles have a particle size of 0.05 to 20 $\mu$m, more preferably from 0.1 to 10 $\mu$m in the pressure-sensitive adhesive layer. Such a particle size may be determined taking into account the swelling ratio of the crosslinked particles swelled with a solvent.

Also, as described above, a state in which the crosslinked acrylic copolymer particles are contained in an acrylic copolymer solution can be made by adding the crosslinking agent to an acrylic copolymer solution, applying a crosslinking treatment to a part of the acrylic copolymer and then pulverizing the resulting product. The obtained solution having such a state as such can be used in forming a pressure-sensitive adhesive layer. The continuous process from the acrylic copolymer preparation can provide a pressure-sensitive adhesive layer containing crosslinked acrylic copolymer particles and is convenient since the production steps are simplified.

In this case, the crosslinking percentage (gel percentage) at the time of the completion of the crosslinking reaction is equal to the content of the crosslinked acrylic copolymer particles of the pressure-sensitive adhesive layer. Accordingly, the preferred content ratio described above can be obtained by adjusting the amount of the crosslinking agent or the time of the crosslinking reaction and thereby controlling the gel percentage of the acrylic copolymer. For instance, in the case where the gel percentage is controlled to 50 to 60% by weight, the remaining unreacted acrylic copolymer becomes 40 to 50% by weight. Thus, the desired content ratio can be achieved easily.

The pressure-sensitive adhesive layer of the percutaneous absorption preparation of the present invention can contain various additives which include not only drugs for percutaneous absorption use but also percutaneous penetration enhancers and other additives such as antioxidants. It is desirable to add these additives in the acrylic copolymer solution containing crosslinked acrylic copolymer particles.

As the percutaneous penetration enhancer, various compounds can be used, which include a compound that has a function to improve solubility and dispersibility of drugs in the pressure-sensitive adhesive layer, a compound that has a function to improve percutaneous absorption by improving keratin moisture holding ability, keratin softening ability or keratin permeability (loosening), by acting as a permeation enhancer or pore opening agent or by changing surface conditions of the skin and a compound that has these functions simultaneously, and a compound which is possessed of not only these functions but a drug effect improving function to further increase efficacy of drugs.

These percutaneous penetration enhancers are exemplified below:

glycols such as diethylene glycol, propylene glycol, and polyethylene glycol as a compound which mainly improves drug solubility;

oils and fats such as olive oil, squalene and lanolin as a compound which mainly improves drug dispersibility;

urea derivatives such as urea and allantoin as a compound which mainly improves moisture holding ability of keratin;

polar solvents such as dimethyldecyl phosphoxide, methyloctyl sulfoxide, dimethyllaurylamide, dodecylpyrrolidone, isosorbitol, dimethylacetamide, dimethyl sulfoxide and dimethylformamide as a compound which mainly improves keratin permeability;

salicylic acid which mainly improves keratin softening ability;

amino acids mainly as a permeability enhancer;

benzyl nicotinate mainly as a pore opening agent;

sodium lauryl sulfate mainly having a function to change surface conditions of the skin; and salocolum which is jointly used with a drug having excellent percutaneous absorption.

Also useful are a plasticizer such as diisopropyl adipate, phthalic acid esters and diethyl sebacate, hydrocarbons such as liquid paraffin, various emulsifiers, ethoxidized stearyl alcohol, glycerol monoesters such as oleic acid monoglyceride, caprylic acid monoglyceride and lauric acid monoglyceride, higher fatty acid esters such as glycerol diesters, glycerol triesters or a mixture thereof, isopropyl myristate and octyl palmitate, and higher fatty acids such as oleic acid and caprylic acid.

These percutaneous penetration enhancers may be used as a mixture of two or more, and a particularly preferred percutaneous penetration enhancer is a combination of isopropyl myristate with caprylic acid monoglyceride. The percutaneous penetration enhancer is used in a total amount of preferably from 150 to 400 parts by weight, more preferably from 200 to 300 parts by weight, based on 100 parts by weight of the acrylic copolymer. If the amount thereof is smaller than 150 parts by weight, there is a possibility that no sufficient effect as the percutaneous penetration enhancer may be obtained, and if it is larger than 400 parts by weight, stringiness and adhesive residue due to plasticization of the pressure-sensitive adhesive layer may be caused. Also, the addition in an unnecessarily large amount does not bear proportionally increased effect as a percutaneous penetration enhancer in most cases and is not desirable from the economical point of view.

Also, it is desirable that these percutaneous penetration enhancers have good compatibility with the acrylic copolymer and crosslinked acrylic copolymer particles, because their compatibility with these percutaneous penetration enhancers renders possible addition of a soft feeling to the resulting preparation, improvement of its adhesion and percutaneous absorption and reduction of skin irritation.

The drug for percutaneous absorption to be contained in the aforementioned pressure-sensitive adhesive layer is not particularly limited, provided that it has percutaneous absorption property. Examples thereof include a general anesthetic drug, a hypnotic sedative, an antiepileptic, an antipyretic-analgesic-anti-inflammatory drug, an antivertigo drug, a drug for psychoneurosis, a neuromuscular junction blocking drug, a drug for autonomic nerve, an antispasmodic, an antiparkinsonism drug, an antihistaminic, a cardiotonic, an arrhythmia treating drug, a diuretic, an antihypertensive drug, a vasoconstrictor, a coronary vasodilator, a peripheral vasodilator, a drug for arteriosclerosis use, a circulatory drug, a respiration enhancer, an antitussive expectorant, a hormone drug, an external drug for purulent disease use, a drug for analgesic, anti-itch, astringent and anti-inflammation use, a drug for parasitic skin disease use, a hemostatic, a gout treating agent, an antidiabetic drug, a drug for malignant tumor treating use, an antibiotic, a chemotherapeutic drug, a narcotic and the like.

The amount of the drug for percutaneous absorption use can be arbitrarily determined depending on the kind of each drug to be used and its administration purpose. The drug may be contained in the pressure-sensitive adhesive layer in an amount of preferably from 1 to 60% by weight, more preferably from 5 to 30% by weight. If the amount thereof is smaller than 1% by weight, there is a possibility of exhibiting no sufficient release of the drug necessary for the therapeutic or preventive purpose, and if it is larger than 60% by weight, there is a possibility that the addition exhibits no proportionally greater effect and results in economical disadvantage, and in some cases, adhesive property to the skin is reduced. According to the present invention, it is not necessary to dissolve the entire amount of the drug for percutaneous absorption use added in the pressure-sensitive adhesive layer, and the drug may be incorporated in an excess amount exceeding the solubility in the pressure-sensitive adhesive layer, so that part of the drug is dispersed in the layer at undissolved state.

The present invention is an effective means particularly in the case where a crosslinking inhibitor is present in the pressure-sensitive adhesive layer. In the prior art percutaneous absorption preparations, optimum pressure-sensitive adhesive characteristics are obtained by making the pressure-sensitive adhesive layer into so-called gel state through crosslinking of the entire portion of the adhesive layer using chemical crosslinking agent such as a trifunctional isocyanate, a metal alcoholate comprised of titanium or aluminum or a metal chelate compound. However, in the case where a crosslinking inhibitor is present in the pressure-sensitive adhesive layer, the crosslinking reaction is inhibited and sufficient pressure-sensitive adhesive characteristics cannot be obtained. Even in such a case, the present invention can provide optimum pressure-sensitive adhesive characteristics by incorporating the crosslinked acrylic copolymer particles in the pressure-sensitive adhesive layer.

Examples of the crosslinking inhibitor against multifunctional isocyanates include a compound having a hydroxyl group, an amino group, a carboxyl group or a mercapto group. Examples of the compound having hydroxyl group include: alcohols such as methanol and ethanol; glycols such as diethylene glycol, propylene glycol and polyethylene glycol; glycerol monoesters such as oleic acid monoglyceride, caprylic acid monoglyceride and lauric acid monoglyceride; glycerol diesters; silica such as hydrated silicon dioxide and soft silicic anhydride; polyhydric alcohols such as glycerol; and water. Examples of the amino group-containing compound and the carboxyl group-containing compound include an amino acid and a fatty acid, respectively.

Also, the examples of the crosslinking inhibitors against metal alcoholates comprised of titanium or aluminum and metal chelate compounds include various compounds such as water, alcohols, diketones, ketoesters, diesters, fatty acids, acid anhydrides, various esters, hydrogen chloride, and amino acids.

In some cases, a percutaneous penetration enhancer or a drug for percutaneous absorption use to be contained in the percutaneous absorption preparation of the present invention functions as a crosslinking inhibitor. The amount effective to be functioned as a crosslinking inhibitor varies depending on the enhancer or drug and other additives, but the crosslinking inhibition action is strongly generated in most cases when the material is contained in the pressure-sensitive adhesive layer in an amount of 10% by weight or more. When such a material is contained in an amount of 70% by weight or more, it acts not only as a crosslinking inhibitor but also as a plasticizer, so that adhesive property becomes poor, shape-keeping ability disappears and stringiness and adhesive residue occur. Particularly, when a fatty acid monoglyceride such as caprylic acid monoglyceride is blended in the pressure-sensitive adhesive layer, the fatty acid monoglyceride is transferred into a separator to cause poor peeling ability of the pressure-sensitive adhesive layer from the separator.

Thus, according to the present invention, these problems can be resolved by incorporating the crosslinked acrylic copolymer particles in the pressure-sensitive adhesive layer, and release of drugs can be controlled easily by adding various percutaneous penetration enhancers.

EXAMPLES

Examples of the present invention are given below by way of illustration and not by way of limitation. The percutaneous absorption preparation of the present invention was prepared in the following manner to confirm the effects of the present invention. In the following, the term "part" means part by weight, and the term "%" means % by weight.

Inventive Example 1
Preparation of Acrylic Copolymer Solution

Firstly, an acrylic copolymer solution was prepared as follows in order to prepare an acrylic copolymer and crosslinked acrylic copolymer particles, both necessary for forming a pressure-sensitive adhesive layer.

Ninety-five parts of 2-ethylhexyl acrylate, 5 parts of acrylic acid, and 0.2 part by weight of benzoyl peroxide were charged into a four-necked flask, the temperature of the contents was raised to 62° to 65° C. in an atmosphere of an inert gas to initiate polymerization reaction, and 125 parts of ethyl acetate was added dropwise to effect the reaction for 8 hours while controlling the reaction temperature, followed by ripening at 75° to 80° C. for 2 hours, thereby obtaining an acrylic copolymer solution.

In an atmosphere of an inert gas such as nitrogen gas, 95 parts of 2-ethylhexyl acrylate and 5 parts of acrylic acid were copolymerized in the ordinary manner in ethyl acetate, thereby preparing an acrylic copolymer solution containing an acrylic copolymer.
Preparation of Pressure-sensitive Adhesive Solution Containing Crosslinked Acrylic Copolymer Particles A trifunctional isocyanate (Coronate HL, manufactured by Nippon Polyurethane Industry Co., Ltd.; the same shall apply hereinafter) was added to the thus obtained acrylic copolymer solution in an amount of 0.13 part per 100 parts of the acrylic copolymer, and the concentration of the acrylic copolymer was adjusted to 25% by adding ethyl acetate. Thereafter, the resulting mixture was put into an airtight container and subjected to heat aging at 60° C. for 96 hours to prepare a pressure-sensitive adhesive solution containing crosslinked acrylic copolymer. This solution was found to have a gel percentage of 59% when measured by a method which will be described later (all data of the gel percentage shown in the following were obtained by the same method). The weight ratio of the acrylic copolymer and crosslinked acrylic copolymer particles in this pressure-sensitive adhesive solution was found to be 144 parts by weight of the crosslinked acrylic copolymer particles to 100 parts by weight of the acrylic copolymer.

Using a pump for high viscosity use, the thus obtained pressure-sensitive adhesive solution containing crosslinked acrylic copolymer particles was charged into Gorator (manufactured by Nittetsu Mining Co., Ltd.) and pulverized into a particle size of 1 to 2 mm. This was then diluted with ethyl acetate to adjust the concentration of the crosslinked acrylic copolymer particles to 10% and further pulverized using TK Homomixer (manufactured by Tokushu Kika Kogyo K. K.) into a particle size of 1 to 10 μm.

Next, prilocaine and isopropyl myristate were added to the pressure-sensitive adhesive solution containing crosslinked acrylic copolymer particles so as to provide their concentrations of 50% and 10%, respectively, and uniformly dissolved by stirring. The thus-prepared pressure-sensitive adhesive solution was coated and dried on a separator made of polyester (75 μm in thickness) in such an amount that the weight of the pressure-sensitive adhesive became 2 mg/cm² after drying, thereby obtaining a pressure-sensitive adhesive layer. Thereafter, a sheet of polyester film (12 μm in thickness) was laminated as a backing on the pressure-sensitive adhesive layer to obtain a percutaneous absorption preparation.

Inventive Example 2

The pressure-sensitive adhesive solution containing crosslinked acrylic copolymer particles prepared in Inventive Example 1 was mixed with 5% of indeloxazine hydrochloride, 30% of caprylic acid monoglyceride, 10% of isopropyl myristate and 10% of hydrated silicic acid (Carplex #80, manufactured by Shionogi & Co., Ltd.), and the resulting mixture was uniformly dispersed by stirring. The thus prepared pressure-sensitive adhesive solution was coated and dried on the non-woven fabric-side of a laminate film composed of a sheet of polyester non-woven fabric (weight basis: 12 g/m³) and a polyester film (2 μm in thickness) as a backing in such an amount that the amount of the pressure-sensitive adhesive was 4 mg/cm² after drying, thereby obtaining a pressure-sensitive adhesive layer. Thereafter, a sheet of polyester film (12 μm in thickness) was laminated as a separator on the pressure-sensitive adhesive layer, thereby obtaining a percutaneous absorption preparation.

Inventive Example 3

A percutaneous absorption preparation was obtained in the same manner as in Inventive Example 2, except that the trifunctional isocyanate was used in an amount of 0.06 part based on 100 parts by weight of the acrylic copolymer. In this case, gel percentage of the pressure-sensitive adhesive solution was found to be 41%, and the crosslinked acrylic copolymer particles were contained in an amount of 70 parts to 100 parts of the acrylic copolymer.

Inventive Example 4

A percutaneous absorption preparation was obtained in the same manner as in Inventive Example 2, except that the trifunctional isocyanate was used in an amount of 0.17 part based on 100 parts by weight of the acrylic copolymer. In this case, the gel percentage of the pressure-sensitive adhesive solution was found to be 75%, and the crosslinked acrylic copolymer particles were contained in an amount of 300 parts to 100 parts of the acrylic copolymer.

Comparative Example 1

A three neck flask equipped with a stirrer and a reflux condenser was charged with 600 parts of ion-exchanged water and 0.5 part of polyvinyl alcohol (saponification degree, 78.5 to 81.5%) as a dispersing agent, and the contents were thoroughly mixed by stirring. To this solution was added a monomer mixture consisting of 200 parts of 2-ethylhexyl acrylate, 10 parts of acrylic acid and 0.2 part of benzoyl peroxide. In an atmosphere of an inert gas such as nitrogen gas, the thus prepared solution was stirred at 25° C. (300 rpm) for 1 hour and then at 65° C. for 4 to 5 hours to effect copolymerization. This was further heated to 80° C. and stirred for 2 hours to complete the copolymerization reaction, thereby obtaining a pressure-sensitive adhesive solution containing acrylic copolymer particles which have not been crosslinked. This pressure-sensitive adhesive solution contained 25% of acrylic copolymer particles. The pressure-sensitive adhesive solution was then mixed with 600 parts of methanol to recover the precipitated acrylic copolymer particles. The precipitated acrylic copolymer particles were dispersed in ethyl acetate to obtain a dispersion having a concentration of 10%. The particle size of the acrylic copolymer particles at this stage was found to be 5 to 80 μm. Then, prilocaine and isopropyl myristate were added thereto, and a percutaneous absorption preparation was prepared in the same manner as in Inventive Example 1.

Comparative Example 2

To the acrylic copolymer solution obtained in Inventive Example 1 were added prilocaine and isopropyl myristate in such amounts that their final concentrations in the preparation became equal to those of the percutaneous absorption preparation of Inventive Example 1. Next, the trifunctional isocyanate was added thereto such that the concentration was 0.052% (corresponds to 0.13 part per 100 parts of the acrylic copolymer). Thus, the prepared pressure-sensitive adhesive solution was prepared, and a percutaneous absorption preparation containing prilocaine was prepared in the same manner as in Inventive Example 1. Thereafter, the preparation was subjected to heat aging at 70° C. for 60 hours to obtain a percutaneous absorption preparation of Comparative Example 2. In this case, the gel percentage of the pressure-sensitive adhesive solution was 20%, and the amount of the crosslinked acrylic copolymer was about 8% of the entire pressure-sensitive adhesive.

Comparative Example 3

A percutaneous absorption preparation was prepared in the same manner as in Comparative Example 2, except that the trifunctional isocyanate was not added and the heat aging was not carried out. In this case, the gel percentage of the pressure-sensitive adhesive solution was found to be 18%.

Comparative Example 4

A copolymer suspension (Primal N-580 (NF-1), manufactured by Japan Acrylic Chemical Co., Ltd.) obtained in an aminoacetic acid aqueous solution of methacrylic acid and n-butyl acrylate was mixed with the same weight of ethanol to recover the thus precipitated methacrylic acid/n-butyl acrylate copolymer particles. The methacrylic acid/n-butyl acrylate copolymer particles were washed with ethanol and re-dispersed in ethanol to a concentration of 20%. Particle size of the copolymer particles was found to be about 250 to 550 nm. To this solution, were added indeloxazine hydrochloride, caprylic monoglyceride, isopropyl myristate and hydrated silicic acid, and a percutaneous absorption preparation was prepared in the same manner as in Inventive Example 2.

Comparative Example 5

To the acrylic copolymer solution obtained in Inventive Example 1 were added indeloxazine hydrochloride, caprylic monoglyceride, isopropyl myristate and hydrated silicic acid in such amounts that their final concentrations in the preparation became equal to those of the percutaneous absorption preparation of Inventive Example 2. Next, the trifunctional isocyanate was added thereto in such an amount that the concentration was 0.0585% (corresponds to 0.13 part per 100 parts of the acrylic copolymer) to prepare a pressure-sensitive adhesive solution, and a percutaneous absorption preparation containing indeloxazine hydrochloride was prepared in the same manner as in Inventive Example 2. Thereafter, the preparation was subjected to heat aging at 70° C. for 60 hours to obtain a percutaneous absorption preparation of Comparative Example 5. In this case, the gel percentage of the pressure-sensitive adhesive solution was 25%, and the amount of the crosslinked acrylic copolymer was about 11.25% of the entire pressure-sensitive adhesive.

Comparative Example 6

A percutaneous absorption preparation was prepared in the same manner as in Comparative Example 5, except that the trifunctional isocyanate was not added and the heat aging was not carried out. In this case, the gel percentage of the pressure-sensitive adhesive solution was found to be 18%.

Comparative Example 7

A percutaneous absorption preparation was obtained in the same manner as in Inventive Example 2, except that the trifunctional isocyanate was added in an amount of 0.03 part based on 100 parts by weight of the acrylic copolymer. In this case, the gel percentage of the pressure-sensitive adhesive solution was found to be 29%, and the weight ratio of the crosslinked acrylic copolymer particles after pulverization was 40 parts of the crosslinked acrylic copolymer particles to 100 parts of the acrylic copolymer.

Comparative Example 8

A percutaneous absorption preparation was obtained in the same manner as in Inventive Example 2, except that the trifunctional isocyanate was added in an amount of 0.5 part based on 100 parts by weight of the acrylic copolymer. In this case, the gel percentage of the pressure-sensitive adhesive solution was found to be 83%, and the weight ratio of the crosslinked acrylic copolymer particles after pulverization was 500 parts of the crosslinked acrylic copolymer particles to 100 parts of the acrylic copolymer.

Measurement of Gel Percentage

For the measurement of the gel percentage, each of the pressure-sensitive adhesive solutions of acrylic copolymers prepared in the inventive and comparative examples was coated and dried on a backing under ordinary condition for the preparation of a conventional pressure-sensitive adhesive tape, in such an amount that the thickness of the pressure-sensitive adhesive layer after drying became about 40 μm to prepare each sample to be tested by the following method.

A porous film made of tetrafluoroethylene (30 to 100 μm in thickness and 0.1 to 1.0 μm in average pore size) is cut to a piece of 100 mm in width and 200 mm in length, and a sample punched out into a size of 40 $cm^2$ (corresponds to 60 to 200 mg as the weight of pressure-sensitive adhesive) is adhered to the piece of porous film. Next, a bag of the porous film is made by bending the thus-prepared porous film double in such a manner that the sample is not overlapped and then bending each tip of its three corners twice so that crosslinked acrylic copolymer particles leaked out of the sample do not leak from the bag. The thus prepared bag is soaked for 24 hours in 100 ml of a solvent capable of dissolving an acrylic copolymer such as ethyl acetate. This soaking step is repeated twice. Thereafter, the solvent is evaporated and then each of the following weights is measured to calculate the gel percentage based on the following formula.

$$\text{Gel Percentage } (\%) = [(B-C-D-F)/(A-C-D-E)] \times 100$$

A: weight (g) of the porous film bag (including sample) before soaking

B: weight (g) of the porous film bag (including sample) after soaking

C: weight (g) of the porous film

D: weight (g) of the backing

E: weight (g) of the additive

F: weight (g) of the additive remained in the porous film bag after soaking due to incomplete removal by the solvent In this connection, when weight C of the porous film and weight D of the backing vary before and after soaking, changes in the weight of the porous film and the backing are respectively measured in advance, and the gel percentage is corrected based on the weight changes. Also, where additives were contained in the pressure-sensitive adhesive solutions (Comparative Examples 2, 3, 5 and 6) from which the samples were prepared, values converted from the blending ratio of additives were used as weights E and F of the additives.

Comparative Tests

Using the percutaneous absorption preparations obtained in Inventive Examples 1 to 4 and Comparative Examples 1 to 8, the following items were tested (measured). The obtained results are shown in Tables 1, 2 and 3.

tensile tester at a rate of 300 mm/min to its 180 degree direction under conditions of 23° C. and 60% R.H. to measure peeling strength (g).

Holding Powder Test

A 20 mm in length of one tip of each sample of the percutaneous absorption preparations cut into a size of 10 mm in width and 50 mm in length was adhered to a tip of a Bakelite plate, and 150 g of load was applied to the other tip of the sample and then stored at 40° C. The time (minute) until each sample was dropped due to generation of cohesive failure was measured.

Anchor Force Test

The backing side of a placebo tape cut into a size of 13 mm in width and 100 mm in length (a tape prepared from each of percutaneous absorption preparations obtained in the same manner as in the respective Inventive and Comparative Examples except that the drugs and additives were not added) was fixed on a Bakelite plate of 25×100 mm in size using a pressure-sensitive adhesive double coated tape. The pressure-sensitive adhesive layer side of each sample of the percutaneous absorption preparations cut into a size of 12 mm in width and 70 mm in length was adhered to the pressure-sensitive adhesive layer side of the placebo tape using an 850 g load roller and then the sample was immediately peeled off using a Tensilon tensile tester at a rate of 300 mm/min in the 90 degree direction under conditions of 23° C. and 60% R.H. to measure load stress (g).

TABLE 1

|  | Adhesive Force (g/12 mm) | Holding Force (min.) | Holding Force/ Adhesive Force | Anchor Force (g/12 mm) | Adhesion Test | Coating Test |
| --- | --- | --- | --- | --- | --- | --- |
| Inventive Example 1 | 172 | 240 | 1.4 | 510 | A | A |
| Comparative Example 1 | 132 | 22 | 0.17 | 121 | C[*1] | C[*2] |
| Comparative Example 2 | 195 | 28 | 0.14 | 211 | C[*1] | A |
| Comparative Example 3 | 212 | 24 | 0.11 | 203 | C[*1] | A |

[*1]: anchor failure
[*2]: streaked coating and poor appearance

TABLE 2

|  | Adhesive Force (g/12 mm) | Holding Force (min.) | Holding Force/ Adhesive Force | Anchor Force (g/12 mm) | Adhesion Test | Coating Test |
| --- | --- | --- | --- | --- | --- | --- |
| Inventive Example 2 | 23 | 20 | 0.87 | 252[*2] | A | A |
| Comparative Example 4 | 17 | 1.6 | 0.09 | 72[*2] | B[*1] | A |
| Comparative Example 5 | 20 | 1.7 | 0.085 | 270[*1] | C[*1] | A |
| Comparative Example 6 | 23 | 2.0 | 0.087 | 295[*1] | C[*1] | A |

[*1]: cohesive failure
[*2]: partial anchor failure

Adhesive Force Test

Each sample of the percutaneous absorption preparations cut into a zonal shape of 12 mm in width was laminated on a Bakelite plate, adhered by a pressure of one reciprocation of an 850 g load roller and then peeled off using a Tensilon Judgement of Anchor Force In the measurement, the anchor force to the backing was evaluated as a load stress at the time of clean peeling between the backing and pressure-sensitive adhesive layer of each of the percutaneous absorption preparations prepared in Inventive and Comparative Examples. A case was judged as cohesive failure when a failure phenomenon of the pressure-sensitive adhesive layer, such as stringiness, was observed during the measurement due to residual pressure-sensitive adhesive layer on the backing. Also, an intermediate case of the aforementioned phenomenon in which the pressure-sensitive adhesive layer was found partially remaining on the backing was judged as partial anchor failure. In addition, a case in which the pressure-sensitive adhesive layer of each of the percutaneous absorption preparations prepared in Inventive and Comparative Examples and the pressure-sensitive adhesive layer of the placebo tape were cleanly peeled off from each other was judged as interface peeling. A case where a pressure-sensitive adhesive layer is peeled off from the support was judged as anchor failure. It is considered that the percutaneous absorption preparations prepared in Inventive and Comparative Examples have sufficient anchor force and aggregation property when the interface peeling or placebo tape anchor failure is observed.

Human Skin Adhesion Test

Each sample of the percutaneous absorption preparations cut into a size of 30 mm in width and 50 mm in length was adhered to an inside part of a forearm of a healthy volunteer. After 1 hour of the adhesion, the sample was peeled off to observe its anchor failure condition. The evaluation was conducted based on the following criteria.

A: No generation of anchor failure or adhesive residue.
B: Slight generation of anchor failure or cohesive failure on the edge part and residue of the pressure-sensitive adhesive on the skin.
C: Generation of anchor failure or cohesive failure on the entire surface and residue of the pressure-sensitive adhesive on the skin.

Coating Property and Appearance Test

Coating property at the time of coating and appearance of the prepared percutaneous absorption preparations were evaluated based on the following criteria.

A: Smooth coat surface and no abnormal appearance.
B: Slight streaked coating and irregularity on the coat surface, but no particular problems in appearance.
C: Extreme streaked coating and irregularity on the coat surface and not suitable as a preparation due to rough appearance.

Test Results

As it can be seen from the results shown in Table 1, when the percutaneous absorption preparation of Inventive Example 1 is compared with the percutaneous absorption preparations of Comparative Examples 1 to 3, they have almost the same adhesive force, but the percutaneous absorption preparation of Inventive Example 1 was most excellent in terms of the holding force test, showing about 10 times higher improvement in comparison with those of the Comparative Examples, because the acrylic copolymer contained crosslinked acrylic copolymer particles in advance.

It also showed an unexpectedly excellent anchor ability to the backing, and, to our surprise, its anchor force was two times or more higher than the case of the Comparative Examples. Also, the percutaneous absorption preparation of Inventive Example 1 caused no adhesive residue in the human skin adhesion test, showing its practical usefulness. In addition, it showed no problems in terms of coating property because of the pulverization of the crosslinked acrylic copolymer into thin granular form, thus confirming that it was an excellent percutaneous absorption preparation.

On the other hand, in the case of the percutaneous absorption preparation of Comparative Example 1 in which a granular pressure-sensitive adhesive was used, its coating property was unstable in solvents other than water, and its appearance was also poor for practical use. In the case of the percutaneous absorption preparations of Comparative Examples 2 and 3, they showed no problems in terms of coating property and appearance, but good holding force was not obtained. This appears to be because prilocaine acts as a crosslinking inhibitor against the trifunctional isocyanate to cause insufficient crosslinking of the acrylic copolymers. As shown in Table 2, the percutaneous absorption preparations of Inventive Example 2 and Comparative Examples 4 to 6 had almost the same, weak adhesive force, which was weak due to the influence of caprylic acid monoglyceride. The preparation of Inventive Example 2 exhibited excellent performance in the holding force test and no adhesive residue in the human skin adhesion test, proving that the preparation was practical. In the anchor force test, the four preparations exhibited markedly strong anchor force, because of the use of a laminate film made of a polyester non-woven fabric and a polyester film, without any preparation evaluated as complete anchor failure. However, the percutaneous absorption preparation of Inventive Example 2 did not exhibit a large quantity of stringiness caused by cohesive failure which Comparative Examples 5 and 6 exhibited, and exhibited the anchor force about 3.5 times that of Comparative Example 4. Thus, it was confirmed that the percutaneous absorption preparation of Inventive Example 2 was excellent.

The phenomenon of a large quantity of stringiness suggests that caprylic acid monoglyceride and hydrated silicic acid acted to inhibit the crosslinking of the acrylic copolymers in the compositions of the percutaneous absorption preparations of Comparative Examples 5 and 6. Particularly, the percutaneous absorption preparation of Comparative Example 4, in which a granular pressure-sensitive adhesive was used, exhibited excellent coating property as compared with that of Comparative Example 1, but exhibited low cohesive force (holding force) and adhesive residue generated on the edge part in the human skin adhesion test.

TABLE 3

|  | Content of Crosslinked Particles (parts) | Adhesive Force (g/12 mm) | Holding Force (min.) | Holding Force/ Adhesive Force | Anchor Force (g/12 mm) | Adhesion Test | Coating Test |
|---|---|---|---|---|---|---|---|
| Comparative Example 7 | 40 | 30 | 2 | 0.07 | 300*2 | C*1 | A |
| Inventive Example 3 | 70 | 26 | 8 | 0.31 | 270*1 | A | A |
| Inventive | 144 | 23 | 20 | 0.87 | 252*2 | A | A |

TABLE 3-continued

|  | Content of Crosslinked Particles (parts) | Adhesive Force (g/12 mm) | Holding Force (min.) | Holding Force/ Adhesive Force | Anchor Force (g/12 mm) | Adhesion Test | Coating Test |
|---|---|---|---|---|---|---|---|
| Example 2 |  |  |  |  |  |  |  |
| Inventive Example 4 | 300 | 20 | 22 | 1.10 | 100*2 | A | A |
| Comparative Example 8 | 500 | 15 | ≧30*3 | — | 75*2 | B*2 | B |

*1: anchor failure
*2: partial anchor failure
*3: The sample slipped down and the accurate holding force could not be measured.

Table 3 shows the comparison of percutaneous absorption preparations having different amounts of crosslinked acrylic copolymer particles. The term "crosslinked particle content" used in Table 3 means the content (parts by weight) per 100 parts by weight of acrylic copolymer. As seen from the results shown in Table 3, the percutaneous absorption preparations of Inventive Examples 2 to 4 were excellent in cohesive force because of the high holding force, as compared with that of Comparative Example 7, and were excellent in adhesive force, anchor force and coating property, as compared with that of Comparative Example 8, and exhibited the excellent results in terms of their stringiness and anchor force in the human skin adhesion test. Thus, it was confirmed that the percutaneous absorption preparations of Inventive Examples 2 to 4 were practically useful.

FIG. 1 shows the relationship between the content ratio of crosslinked acrylic copolymer particles and the physical properties of the percutaneous absorption preparations of Inventive Examples 2 to 4 and Comparative Examples 7 and 8. In the drawing, open circles indicate adhesive force, saltires indicate holding force and open triangles indicate the ratio of holding force to adhesive force (holding force/adhesive force). According to this drawing, 100 parts by weight or more of crosslinked acrylic copolymer particles are contained in 100 parts by weight of the acrylic copolymer in a preparation having well-balanced holding force/adhesive force value of 0.5 or more.

Figure 2:
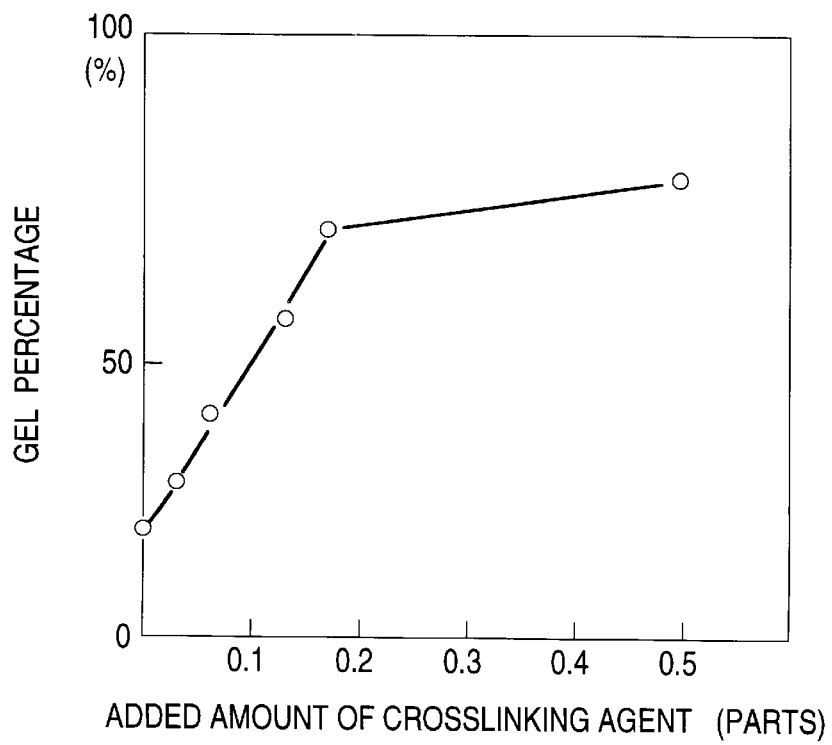
FIG. 2 is a graph showing a relationship between amount of a crosslinking agent added to an acrylic copolymer and gel percentage of a pressure-sensitive adhesive solution containing crosslinked acrylic copolymer particles.

FIG. 2 shows the relationship between the added amount of a crosslinking agent and the gel percentage of a pressure-sensitive adhesive solution containing crosslinked acrylic copolymer particles, which indicates that the amount of the added crosslinking agent exceeding 0.7 part by weight per 100 parts by weight of the acrylic copolymer before crosslinking (corresponds to 300 parts by weight of the crosslinked acrylic copolymer particles) is not effective in proportionally improving formation ratio of the crosslinked acrylic copolymer particles.

From these results, it can be seen that a preparation having a holding force/adhesive force value of 0.5 or more, preferably close to 1 shows well-balanced relation between the adhesive force and cohesive force and therefore is an excellent adhesion type percutaneous absorption preparation which does not practically cause stringiness and adhesive residue. From the results of the human skin adhesion test, it can be seen that the crosslinked acrylic copolymer particles should be 70 parts by weight or more as the practical level, but preferably 400 parts by weight or less from the point of view of coating property.

As described above, the percutaneous absorption preparations obtained in Inventive Examples 1 to 4 are practically markedly excellent percutaneous absorption preparations which show well-balanced relation between the adhesive force and cohesive force, have a soft touch because of the incorporation of a percutaneous penetration enhancer, namely have less irritation to the skin, and exert high pharmacological activities due to its absorption enhancing effect.

The pressure-sensitive adhesive layer of the percutaneous absorption preparation according to the present invention comprises an acrylic polymer containing therein crosslinked acrylic copolymer particles prepared by crosslinking and pulverizing an acrylic copolymer, and the cohesive force of the pressure-sensitive adhesive layer can be increased and a percutaneous absorption preparation being excellent in coating property and appearance can be provided.

In addition, since a percutaneous absorption preparation which is also excellent in anchor force can be obtained, with reduced generation of stringiness and adhesive residue.

In the case where a drug for percutaneous absorption use or a percutaneous penetration enhancer has crosslinking inhibition action, the preparation according to the present invention is especially effective, and the pressure-sensitive adhesive characteristics can be controlled without being affected by crosslinking inhibitors. For example, the present invention is suitable in the case where a fatty acid monoglyceride is added as a percutaneous penetration enhancer. Namely, various drugs can be used without being influenced by the drugs for percutaneous absorption use and percutaneous penetration enhancers, and by using various percutaneous penetration enhancers, release control of the drugs can be facilitated and the range of application of the percutaneous absorption preparation can be widened.

According to the method for the production of the percutaneous absorption preparation of the present invention, a pressure-sensitive adhesive solution containing crosslinked acrylic copolymer particles is prepared by adding a crosslinking agent to an acrylic copolymer solution and crosslinking and pulverizing the copolymer. The pressure-sensitive adhesive solution in which crosslinked particles are formed can be used as such without taking out the crosslinked acrylic copolymer particles. The pressure-sensitive adhesive solution is blended with a drug for percutaneous absorption use and other necessary additives, and coated on a backing to form a pressure-sensitive adhesive layer. Accordingly, the preparation can be produced continuously from the preparation of the acrylic copolymer without complicating the production steps.

While the invention has been described in detail with reference to specific embodiments, it will be apparent to one skilled in the art that various changes and modifications can be made to the invention without departing from its spirit and scope.

What is claimed is:

1. A percutaneous absorption preparation comprising a backing having formed on one side thereof a pressure-sensitive adhesive layer containing a drug for percutaneous absorption use, wherein the pressure-sensitive adhesive layer contains (A) an acrylic copolymer which is an acrylic pressure-sensitive adhesive and (B) crosslinked acrylic copolymer particles prepared from an acrylic pressure-sensitive adhesive, wherein the crosslinked particles have a size of from about 0.05 to about 20 microns and are present in an amount of from about 70 to about 400 parts by weight of the acrylic copolymer.

2. The percutaneous absorption preparation of claim 1, wherein the crosslinked acrylic copolymer particles are those prepared by subjecting an acrylic copolymer to crosslinking and pulverization.

3. The percutaneous absorption preparation of claim 1, wherein the pressure-sensitive adhesive layer further contains a percutaneous penetration enhancer.

4. The percutaneous absorption preparation of claim 1, wherein the pressure-sensitive adhesive layer further contains a fatty acid monoglyceride as a percutaneous penetration enhancer.

5. The percutaneous absorption preparation of claim 2, wherein the pressure-sensitive adhesive layer further contains a percutaneous penetration enhancer.

6. The percutaneous absorption preparation of claim 2, wherein the pressure-sensitive adhesive layer further contains a fatty acid monoglyceride as a percutaneous penetration enhancer.

7. A method for producing a percutaneous absorption preparation comprising a backing having formed on one side thereof a pressure-sensitive adhesive layer containing a drug for percutaneous absorption use, which comprises:

adding a crosslinking agent to a solution of an acrylic copolymer to effect crosslinking, pulverizing the resulting solution to prepare a pressure-sensitive adhesive solution, adding a drug for percutaneous absorption use and optionally a percutaneous penetration enhancer to the pressure-sensitive adhesive solution, and coating the backing with the resulting pressure-sensitive adhesive solution to form a pressure-sensitive adhesive layer.

* * * * *